United States Patent
Li et al.

(10) Patent No.: US 11,234,910 B2
(45) Date of Patent: *Feb. 1, 2022

(54) CAPSULES COMPRISING PIGMENTS, AND METHOD FOR PRODUCING SAME

(71) Applicant: AMOREPACIFIC CORPORATION, Seoul (KR)

(72) Inventors: Yan Li, Yongin-si (KR); Hyun Suk Lee, Yongin-si (KR); Sun Kyung Choi, Yongin-si (KR); Yong Jin Kim, Yongin-si (KR); John Hwan Lee, Yongin-si (KR); Eun Jeong Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/338,392

(22) PCT Filed: Sep. 26, 2017

(86) PCT No.: PCT/KR2017/010589
§ 371 (c)(1),
(2) Date: Mar. 29, 2019

(87) PCT Pub. No.: WO2018/062803
PCT Pub. Date: Apr. 5, 2018

(65) Prior Publication Data
US 2020/0022888 A1    Jan. 23, 2020

(30) Foreign Application Priority Data

Sep. 30, 2016    (KR) .................. 10-2016-0126873
Sep. 25, 2017    (KR) .................. 10-2017-0123425

(51) Int. Cl.
*A61K 8/11*    (2006.01)
*A61K 8/04*    (2006.01)
(Continued)

(52) U.S. Cl.
CPC .................. *A61K 8/11* (2013.01); *A61K 8/04* (2013.01); *A61K 8/25* (2013.01); *A61K 8/29* (2013.01);
(Continued)

(58) Field of Classification Search
CPC ... A16K 8/11; A61K 8/11; A61K 8/04; A61K 8/25; A61K 8/29; A61K 8/362;
(Continued)

(56) References Cited

U.S. PATENT DOCUMENTS

2003/0125222 A1*  7/2003  Jahns ................ C11D 17/0039
                                                            510/130
2005/0069704 A1   3/2005  Rathschlag et al.
(Continued)

FOREIGN PATENT DOCUMENTS

CN    104418972 A    3/2015
CN    105062134 A    11/2015
(Continued)

OTHER PUBLICATIONS

International Search Report for PCT/KR2017/010589 dated Jan. 31, 2018 (PCT/ISA/210).
(Continued)

*Primary Examiner* — Hong Yu
(74) *Attorney, Agent, or Firm* — Sughrue Mion, PLLC

(57) ABSTRACT

The present invention relates to a capsule comprising a pigment and a method for producing the same. More specifically, the present invention relates to a capsule which comprises therein a pigment inside which is likely to be discolored due to external environment, and thereby can (Continued)

easily crack or break and cause color development when applied to the skin, while isolating the pigment from the external environment, and a method for producing the same.

14 Claims, 11 Drawing Sheets

(5 of 11 Drawing Sheet(s) Filed in Color)

(51) Int. Cl.
 A61K 8/25 (2006.01)
 A61K 8/29 (2006.01)
 A61K 8/34 (2006.01)
 A61K 8/362 (2006.01)
 A61Q 1/06 (2006.01)
 A61Q 1/08 (2006.01)
(52) U.S. Cl.
 CPC ............ *A61K 8/345* (2013.01); *A61K 8/362* (2013.01); *A61Q 1/06* (2013.01); *A61Q 1/08* (2013.01); *A61K 2800/43* (2013.01); *A61K 2800/56* (2013.01)
(58) Field of Classification Search
 CPC ............... A61K 8/345; A61K 2800/56; A61K 2800/43; A61Q 1/06; A61Q 1/08
 See application file for complete search history.

(56) References Cited

U.S. PATENT DOCUMENTS

| | | | |
|---|---|---|---|
| 2014/0356403 | A1 | 12/2014 | Zhu et al. |
| 2016/0170091 | A1 | 6/2016 | Li et al. |
| 2016/0367449 | A1 | 12/2016 | Son et al. |
| 2020/0022887 | A1* | 1/2020 | Kim .................. A61Q 1/06 |

FOREIGN PATENT DOCUMENTS

| | | | |
|---|---|---|---|
| EP | 2 939 653 A1 | | 11/2015 |
| JP | 6-100416 A | | 4/1994 |
| JP | 2011-520001 A | | 7/2011 |
| KR | 10-2013-0079244 A | | 7/2013 |
| KR | 10-1342958 B1 | | 12/2013 |
| KR | 10-2014-0113728 A | | 9/2014 |
| WO | WO 01/49817 A2 | * | 7/2001 |
| WO | 03/037995 A1 | | 5/2003 |
| WO | 2009135791 A1 | | 11/2009 |
| WO | 2015/044306 A1 | | 4/2015 |
| WO | 2015/166459 A1 | | 11/2015 |
| WO | WO 2017/085446 A1 | * | 5/2017 |

OTHER PUBLICATIONS

Schilling et al., "Citric acid as a solid-state plasticizer for Eudragit RS PO", Journal of Pharmacy and Pharmacology, 2007, vol. 59, pp. 1493-1500 (8 pages total).
International Searching Authority, International Search report dated Jan. 15, 2018 in application No. PCT/KR2017/010919.

\* cited by examiner (a) capsules comprising pigments (b) capsules rubbed with fingers

| Composition content | Raw Data | Rubbed 3 times | Rubbed 7 times |
|---|---|---|---|
| Example 1 |  |  |  |
| Example 2 |  |  |  |
| Example 3 |  |  |  |

Before formulation test (a) and after formulation test (b)

(a)          (b)

CAPSULES COMPRISING PIGMENTS, AND METHOD FOR PRODUCING SAME

CROSS REFERENCE TO RELATED APPLICATIONS

This application is a National Stage of International Application No. PCT/KR2017/010589 filed Sep. 26, 2017, claiming priority based on Korean Patent Application No. 10-2016-0126873, filed Sep. 30, 2016, and Korean Patent Application No. 10-2017-0123425, filed Sep. 25, 2017.

TECHNICAL FIELD

The present invention relates to a capsule comprising a pigment and a method for producing the same. More specifically, the present invention relates to a capsule which comprises therein a pigment which is likely to be discolored due to external environment, and thereby can easily crack or break and cause color development when applied to the skin, while isolating the pigment from the external environment, and a method for producing the same.

BACKGROUND ART

Pigments are of great importance in the cosmetic field, where altering skin and hair color for aesthetic purposes can be desirable.

However, some pigments used in cosmetics have problems in that when applied to cosmetics requiring various environments, they are already discolored during a formulation process due to unstable properties of the dye itself, or have weak stability against light. Thus, in order to solve such problems, various methods such as emulsification, encapsulation and the like have been developed.

Meanwhile, the capsule applied to cosmetics should be easily cracked or broken under pressure when a user applies to a skin according to its use, so that the pigment contained in the capsule can be easily expressed.

That is, there is a need for a capsule which can effectively isolate a pigment from external environment and thus exhibits excellent storage durability, color hiding power, etc., and which can be easily cracked or broken by pressing, rubbing, wiping or scrubbing with a hand or a tool (cotton cloth, sponge, paper, brush, etc.), thereby allowing the pigment included therein to develop color sufficiently.

DETAILED DESCRIPTION OF THE INVENTION

Technical Problem

In order to solve the above-mentioned problems, the present inventors have developed a spherical capsule structure in which silica and a pigment are mixed by using a polymer as a binder, in order that the capsule is stable at a high temperature and does not easily crack or break during the formulation process and thereby stably maintains the pigment, but when the formulation is applied to the skin, the capsule breaks and thereby causes color development.

Therefore, it is one object of the present invention to provide a capsule structure including a pigment, capable of causing color development of the pigment only when applied to the skin, while protecting the pigment from the external environment and ensuring the stability of the pigment.

Technical Solution

In order to achieve the object above, one aspect of the present disclosure provides a pigment capsule including a pigment, wherein the capsule has an interior in which silica, a pigment and a titanium dioxide pigment are dispersed, and an exterior covered with a polymer binder having a glass transition temperature of 130° C. or higher, and wherein a $C_3$-$C_9$ trivalent carboxylic acid is contained in the interior of the capsule, and a method for producing the same.

Advantageous Effects

The capsule of the present invention can solve the problem related to instability of the pigment against the environment by completely isolating the pigment from the external environment, and also, the capsule is stable during the formulation process, but when applied to the skin, it is easily cracked or broken by force applied while rubbing or scrubbing with a hand or a tool, thereby causing color development easily.

Further, the color development of the pigment is blocked and thus the color due to pigment does not appear in the product, but the color development occurs after the capsule is applied to the skin, which may arouse users' interests when using the product.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
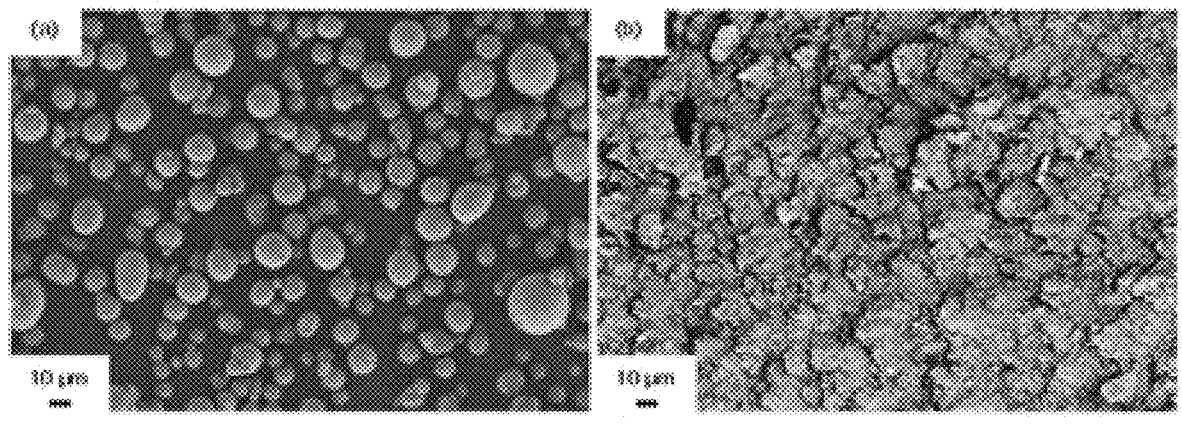
FIG. 1 shows images of the capsules including pigments prepared according to the present invention (a) and the state of capsules that have been broken by rubbing with fingers (b), taken with a scanning electron microscope (SEM).

The present invention provides a pigment capsule including a pigment wherein silica, a pigment and a titanium dioxide pigment are dispersed in an interior of the capsule and wherein an exterior of the capsule is covered with a polymer binder, and a method for producing the same.

In particular, the pigment capsule of the present invention is characterized by having physical properties of maintaining its stability during formulation or storage of the formulated products, but being easily cracked or broken by the pressure at the moment of application to the skin.

The pigment capsule of the present invention has an average diameter of 10 to 15 μm, preferably 10 to 12 μm, and the pigment capsule according to the present invention may be easily cracked or broken, ruptured, dissolved or disintegrated by a small pressure, that is, the pressure generally applied when pressed, rubbed, wiped or scrubbed with a hand or a tool (cotton cloth, sponge, brush, etc.).

In the present invention, in particular, fumed silica (silica dimethyl silylate) is used as the silica.

In addition, in order to increase the hardness of the capsule for the purpose of completely isolating the pigment from the external environment and securing physical stability thereof, by using a polymer binder, the present invention provides a capsule in which a pigment and silica are dispersed inside thereof, and a barrier membrane from the exterior is formed by the polymer binder.

In many cases, a makeup cosmetic composition is subjected to a high temperature during the formulation process, and in particular, a composition for lip makeup such as lipstick is mainly formulated at a high temperature (for example, 95° C. or higher) due to the nature of the mixing process of raw materials, and thus it is very important to secure thermal stability of the capsule. Therefore, as a polymer binder in the present invention, those having a glass transition temperature (Tg) of 130° C. or higher are used.

In addition, the purpose of the pigment capsule in the present invention is that discoloration of the pigment in the capsule does not occur until the product is applied by a user, and thus, the discoloration of the pigment should not occur due to the polymer used.

Therefore, the polymer binder used in the present invention may be those that do not cause discoloration of the pigment, while having a high glass transition temperature (130° C. or higher). In order to satisfy such a condition, an acrylate copolymer, in particular, a polymethacrylate-based copolymer, is used in the present invention, preferably acrylic acid and acrylate copolymer, more preferably acrylic acid and methacrylate copolymer, and in particular, methacrylic acid and methacrylate copolymer are used.

The polymer binder used in the present invention may be used up to 90% by weight based on the total weight of the capsule. However, when the polymer binder is used in an excessive amount, the contents of silica, titanium dioxide, and pigment become relatively small, so that the shape of the capsule may not be spherical and become distorted, and it may not crack or break when rubbed by a hand. Therefore, in consideration of these factors, the content of the polymer binder is preferably 5 to 20% by weight, more preferably 10 to 20% by weight based on the total weight of the capsule.

The pigment used in the present invention is not particularly limited by its type, such as water-soluble dyes and oil-soluble dyes. For example, the following pigments may be used.

carmin of cochenille;
organic dyes such as azo-based, anthraquinone-based, indigo-based, xanthene-based, pyrene-based, quinoline-based, triphenylmethane-based, fluorane dyes; and
insoluble salts of sodium, potassium, calcium, barium, aluminum, zirconium, strontium, titanium of acid-based dyes such as azo-based, anthraquinone-based, indigo-based, xanthene-based, pyrene-based, quinoline-based, triphenylmethane-based, fluorane dyes, and these dyes may include at least one carboxylic or sulfonic acid group.

As specific examples of organic dyes, those having the following trade names may be mentioned:

D&C Blue No. 4, D&C Brown No. 1, D&C Green No. 5, D&C Green No. 6, D&C Orange No. 4, D&C Orange No. 5, D&C Orange No. 10,
D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1,
FD&C Green No. 3, FD&C Red No. 40, FD&C Yellow No. 5, FD&C Yellow No. 6.

In particular, as the pigment capsule according to the present invention, a pigment such as oil-soluble dye Red 27, which exhibits a difference in color expression under humidity changes and alkaline conditions, thus having poor stability, may also be used.

In the pigment capsule of the present invention, the pigment may be used up to 90% by weight based on the total weight of the capsule. However, when the pigment is used in an excessive amount, the contents of the polymer binder forming the capsule exterior become relatively small, and thus, the pigment cannot be completely protected from the external environment, thereby causing a problem in stability of the pigment. Therefore, in consideration of these factors, the content of the pigment may be preferably 0.00001 to 50% by weight, preferably 10 to 50% by weight based on the total weight of the capsule.

Further, the pigment capsule of the present invention contains a $C_3$-$C_9$ trivalent carboxylic acid, preferably, citric acid, propionic acid, iso-citric acid, aconitic acid, tricarballylic acid, and trimesic acid inside thereof. By containing a $C_3$-$C_9$ trivalent carboxylic acid, the pH of the capsule interior can be maintained under an acidic condition, thereby preventing discoloration of the pigment due to contact with an alkali oil. At this time, the content of the $C_3$-$C_9$ trivalent carboxylic acid is not particularly limited as long as it prevents discoloration of the pigment and thereby does not alter the exterior color of the capsule, and in particular, when formulated into a cosmetic composition for lip makeup, as long as it is suitable for the pH standard of the composition. Preferably, it may be added in an amount of 1 to 20% by weight, preferably 1 to 5% by weight based on the total weight of the capsule. When the amount is less than 1% by weight, it may be insufficient to prevent the discoloration of the pigment, and when the amount is more than 20% by weight, the difference in the effects due to an increase in the content is insignificant.

The present invention provides a method for producing a pigment capsule including a pigment, the method including the steps of:

1) dissolving a polymer binder and a $C_3$-$C_9$ trivalent carboxylic acid in a first solvent and dissolving a pigment in a second solvent, respectively, and then mixing them to allow the pigment to disperse in the polymer binder solution;

2) adding silica and titanium dioxide to the mixed polymer solution in which the pigment is dispersed, and dispersing the mixture;

3) spray drying the solution obtained in step 2); and 4) obtaining spray-dried pigment/polymer binder composite powder particles.

In the method of the present invention, the step of dissolving a polymer binder and a pigment is characterized by dissolving each of the polymer binder and the pigment in different solvents so that the both can be sufficiently, completely dissolved, preferably to the extent of 100%, and then mixing and using them, while preventing color development of the pigment.

As the polymer binder and pigment used in the present invention, those described above can be used.

As the solvent for dissolving the polymer binder, an organic solvent, preferably, at least one organic solvent selected from the group consisting of a $C_1$-$C_4$ lower alcohol (for example, methanol, ethanol, isopropanol, butanol, etc.), acetone, and a mixture thereof, or a mixture of the organic solvent and water, for example, methanol, methanol/water (97:3), ethanol, ethanol/water (6:4), isopropanol, isopropanol/water (97:3), isopropanol/water (6:4), N-butanol, acetone, acetone/water (97:3), acetone/water (6:4), acetone/isopropanol (4:6) may be used, more preferably, ethanol or acetone may be used.

Further, as the solvent for dissolving the pigment, a chlorine-containing hydrocarbon-based organic solvent, preferably chloroform, dichloromethane (DCM), and more preferably dichloromethane (DCM) may be used.

In the method of the present invention, the ratio of the solvent for dissolving the polymer binder to the solvent for dissolving the pigment is about 3:7. When the ratio of the solvent is less than about 3:7 (for example, 1:9, 2:8, etc.), the polymer binder may be precipitated, and when the ratio of the solvent is greater than about 3:7, (for example, 4:6, 5:5, 9:1, etc.), discoloration of the pigment may occur, which is not preferred.

When the polymer binder is dissolved in a solvent, the $C_3$-$C_9$ trivalent carboxylic acid, preferably, citric acid, propionic acid, or tricarballylic acid may be added thereto. By containing the $C_3$-$C_9$ trivalent carboxylic acid, the pH of the capsule interior can be maintained under an acidic condition, thereby preventing discoloration of the pigment due to contact with an alkali oil. At this time, the content of the $C_3$-$C_9$ trivalent carboxylic acid is not particularly limited as long as it prevents discoloration of the pigment and thereby does not alter the exterior color of the capsule, and may be preferably contained in an amount of 1 to 20% by weight based on the total weight of the capsule. When the amount is less than 1% by weight, it may be insufficient to prevent the discoloration of the pigment, and when the amount of more than 20% by weight, the difference in the effects due to an increase in the content is insignificant.

Spray drying may be carried out under the following conditions: Feed rate—amount of air fed to twin-fluid nozzle: 40 L/min, amount of dispersion fed: 100 g/min; Environmental conditions—temperature of dispersion (reaction solution): 25° C., spray dryer inlet temperature: 80° C., spray dryer outlet temperature: 60° C. At this time, spray drying may be performed while stirring the mixed polymer solution continuously through a stirrer.

The pigment capsule prepared according to the present invention isolates the pigment from the external environment and does not cause color development of the pigment before application of the final product, for example, cosmetics, to the skin, and also, it contains titanium dioxide pigment in the pigment capsule to mask the inherent color of the pigment, thereby rendering the color of the formulation itself to become close to colorless. That is, it causes color development when the product which is close to colorless, is applied to the skin, and thus, it is also possible to increase interest and attention during make-up.

MODE FOR CARRYING OUT THE INVENTION

Hereinafter, the constitutions and effects of the present invention will be described in detail by way of Examples and Test Examples shown below. However, these Examples and Test Examples are given for illustrative purposes only to help understanding of the present invention, and the scope of the invention is not intended to be limited to or by these Examples and Test Examples.

Example 1

Preparation of Pigment Capsule (1)

Red 27 Lake (20 g, 10%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 20 g, 10%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or less and mixed with the Red 27 Lake solution. Then, silica (AEROSIL® R972, manufactured by Evonik Degussa; 140 g, 70%) and $TiO_2$ (Purolan® E 171A, manufactured by LANXESS; 10 g, 5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITTUTE, capacity: 10 kg/hr ($H_2O$ basis)) and encapsulated.

Example 2

Preparation of Pigment Capsule (2)

A pigment capsule was prepared in the same manner as in Example 1, except that 40 g (20%) of acrylate copolymer was used.

Example 3

Preparation of Pigment Capsule (3)

A pigment capsule was prepared in the same manner as in Example 1, except that 40 g (20%) of acrylate copolymer was used, and 100 g (50%) of Red 27 Lake was used.

Example 4

Preparation of Pigment Capsule (4)

Red 27 Lake (60 g, 30%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 20 g, 10%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or less and mixed with the Red 27 Lake solution. Then, silica (AEROSIL® R972, manufactured by Evonik Degussa; 100 g, 50%) and $TiO_2$ (Purolan® E 171A, manufactured by LANXESS; 10 g, 5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITTUTE, capacity: 10 kg/hr ($H_2O$ basis)) and encapsulated.

Example 5

Preparation of Pigment Capsule (5)

Red 27 Lake (60 g, 30%) was dispersed in dichloromethane (DCM, 1580 mL). Citric acid (15 g, 7.5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 70 g, 35%) and $TiO_2$ (Purolan® E 171A, manufactured by LANXESS; 25 g, 12.5%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITTUTE, capacity: 10 kg/hr ($H_2O$ basis)) and encapsulated.

Example 6

Preparation of Pigment Capsule (6)

Red 27 Lake (40 g, 20%) was dispersed in dichloromethane (DCM, 1580 mL). Citric acid (10 g, 5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 100 g, 50%) and $TiO_2$ (Purolan® E 171A, manufactured by LANXESS; 20 g, 10%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITTUTE, capacity: 10 kg/hr ($H_2O$ basis)) and encapsulated.

Example 7

Preparation of Pigment Capsule (7)

Red 27 Lake (40 g, 20%) was dispersed in dichloromethane (DCM, 1580 mL). Citric acid (15 g, 7.5%) was dissolved in ethanol (402 mL) heated to 60° C., and then an acrylate copolymer as a polymer binder (Eudragit® L 100, manufactured by Evonik Degussa; 30 g, 15%) was dissolved therein. At this time, the volume ratio of ethanol used for dissolving the polymer binder (excluding the volume of ethanol used for dissolving citric acid) and dichloromethane used for dissolving the pigment was 3:7. The mixed dispersion solution of citric acid and acrylate copolymer was cooled to 25° C. or below and mixed with the Red 27 Lake solution. Then, silica (AEROSIL® R972, manufactured by Evonik Degussa; 85 g, 42.5%) and $TiO_2$ (Purolan® E 171A, manufactured by LANXESS; 30 g, 15%) were added to the mixed dispersion solution, and dispersed as follows: a dispersion vessel was introduced into an ultrasonic dispersion bath and the solution was dispersed for 30 minutes using a disperser. Then, the resultant was dried using a spray dryer (DJE-FCNM 020R, manufactured by DONGJIN TECHNOLOGY INSTITTUTE, capacity: 10 kg/hr ($H_2O$ basis)) and encapsulated.

Test Example 1

Verification of Pigment Impregnation in Capsules

The capsules prepared in Examples and Comparative Examples were observed under a scanning electron microscope (SEM) (FIG. 1).

FIG. 1(a) is an image showing the pigment-supported capsules. By applying the spray drying method, it was possible to support the pigment on the silica and to carry out encapsulation in such a manner that the polymer encapsulates the exterior thereof. Further, it was confirmed through the SEM image shown in FIG. 1(a) that the capsules were formed as porous polymer.

Furthermore, it was confirmed through FIG. 1(b), which showed the state of capsules when the capsules of Example 1 were rubbed with fingers several times, that the pigment was developed as the capsule broke.

Figure 2:
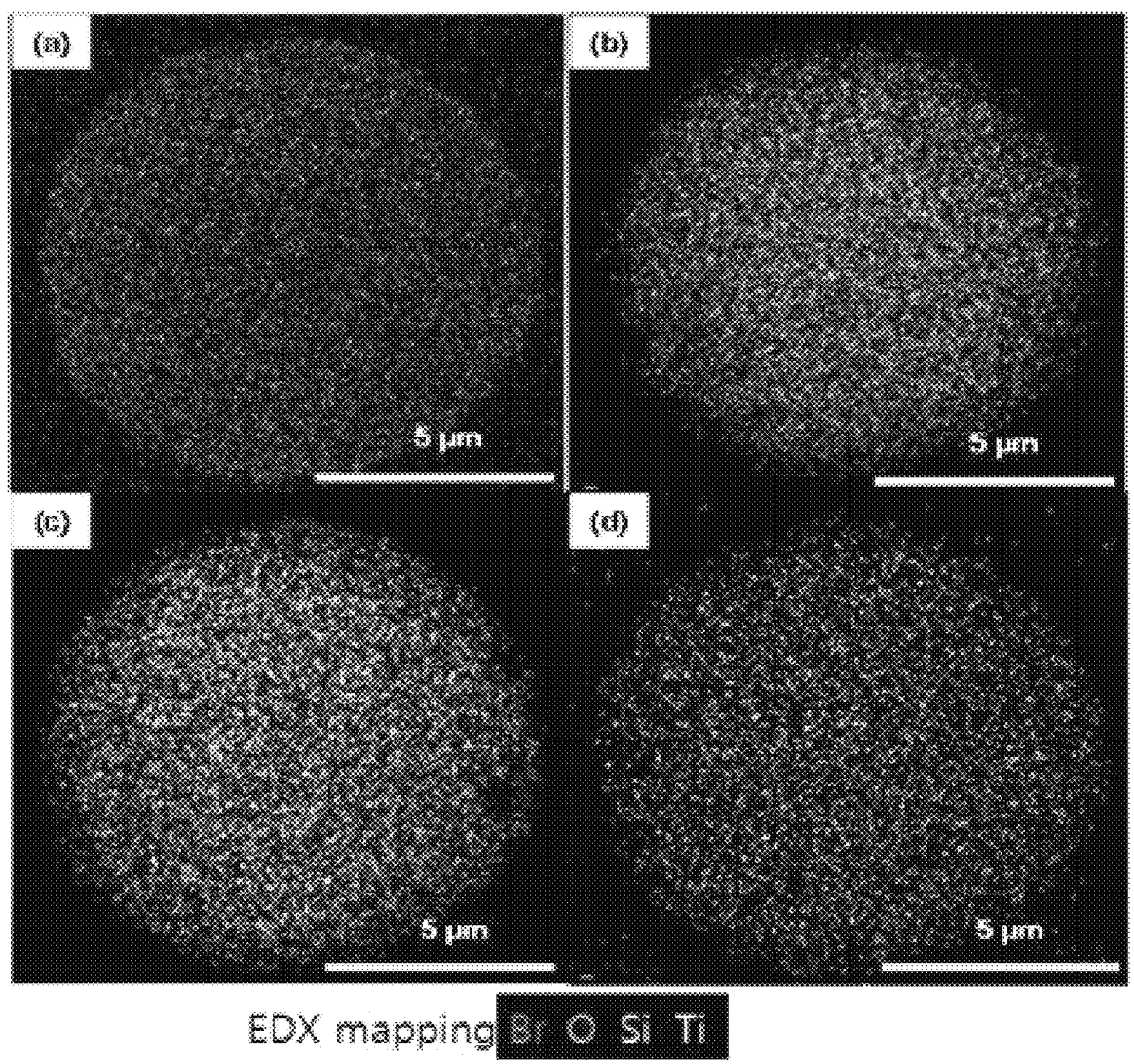
FIG. 2 shows that Si, Ti, O, and Br elements contained in the polymer capsules are evenly distributed through EDX mapping.

In addition, it was confirmed in FIG. 2 that Si, Ti, O, and Br elements contained in the polymer capsules were evenly distributed through EDX mapping, thereby confirming whether or not the pigment was impregnated.

Test Example 2

Determination of Discoloration of Pigment According to the Types of Polymer and the Ratios of the Polymer and Solvent 0.075 g of ethylcellulose, polyvinylpyrrolidone (PVP), polycaprolactone (PCL), polylactic acid (PLA) or poly (methyl methacrylate) as a polymer was dissolved in 5 mL of DCM solution. Then, 0.01 g of Red 27 dye was dissolved in in 5 ml of DCM. The two solutions were separately prepared and then mixed to observe the color change. The observation results are shown in FIG. 3.

Figure 3:
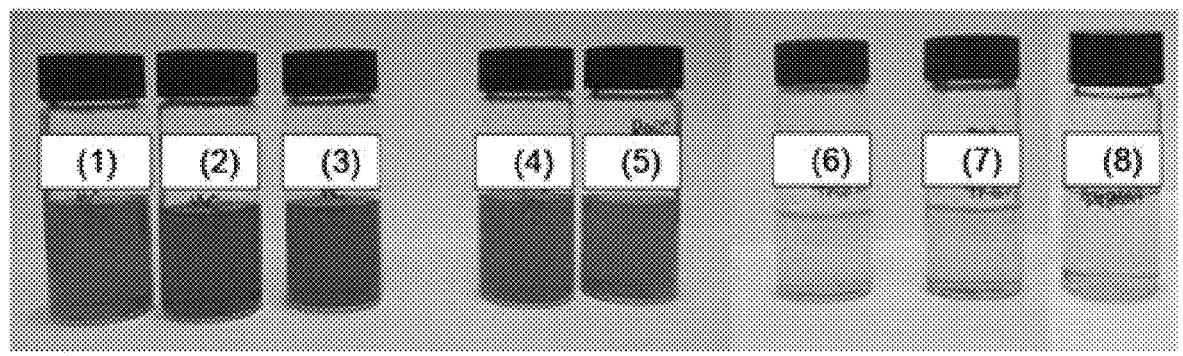
FIG. 3 confirms whether the color development of the pigment occurs depending on the types of the polymer used and the ratio of the polymer and the solvent, or whether the polymer is precipitated ((1) ethyl cellulose 4 cps, (2) ethyl cellulose 100 cps, (3) ethyl cellulose 300 cps, (4) PVP Mw=55000, (5) PVP Mw=360000, (6) PCL, (7) PLA, (8) crosslinked PMMA).

FIG. 3 (1) to (3) show that 4 cps, 100 cps, and 300 cps of ethyl cellulose were used, respectively. As the molecular weight increased, the color became darker.

Meanwhile, FIG. 3 (4) and (5) show that polyvinylpyrrolidone having molecular weights of 55,000 and 360,000 was used, respectively. As the molecular weight of the polyvinylpyrrolidone increased, the color became lighter.

Therefore, although there was a slight difference in color, it was ultimately observed that discoloration occurred regardless of the molecular weight of the polymer.

When PCL, PLA or crosslinked PMMA, which is a different type of polymer binder, was used, there was no discoloration of Red 27 Lake, but the glass transition temperature (Tg) was found to be 105° C. or less. Thus, the stability is not ensured at 95° C. or higher, which is the production temperature for common makeup cosmetics, in particular, cosmetics for lip makeup, and is therefore not suitable for application to the pigment capsules of the present invention (see, FIG. 3 (6) to (8)).

Test Example 3

Evaluation of Stability of Pigment Capsules at High Temperature

In general, makeup cosmetics, in particular, lip makeup cosmetics, are manufactured at high temperatures, thus, it was confirmed whether the capsules maintain stability at high temperatures.

Figure 4:
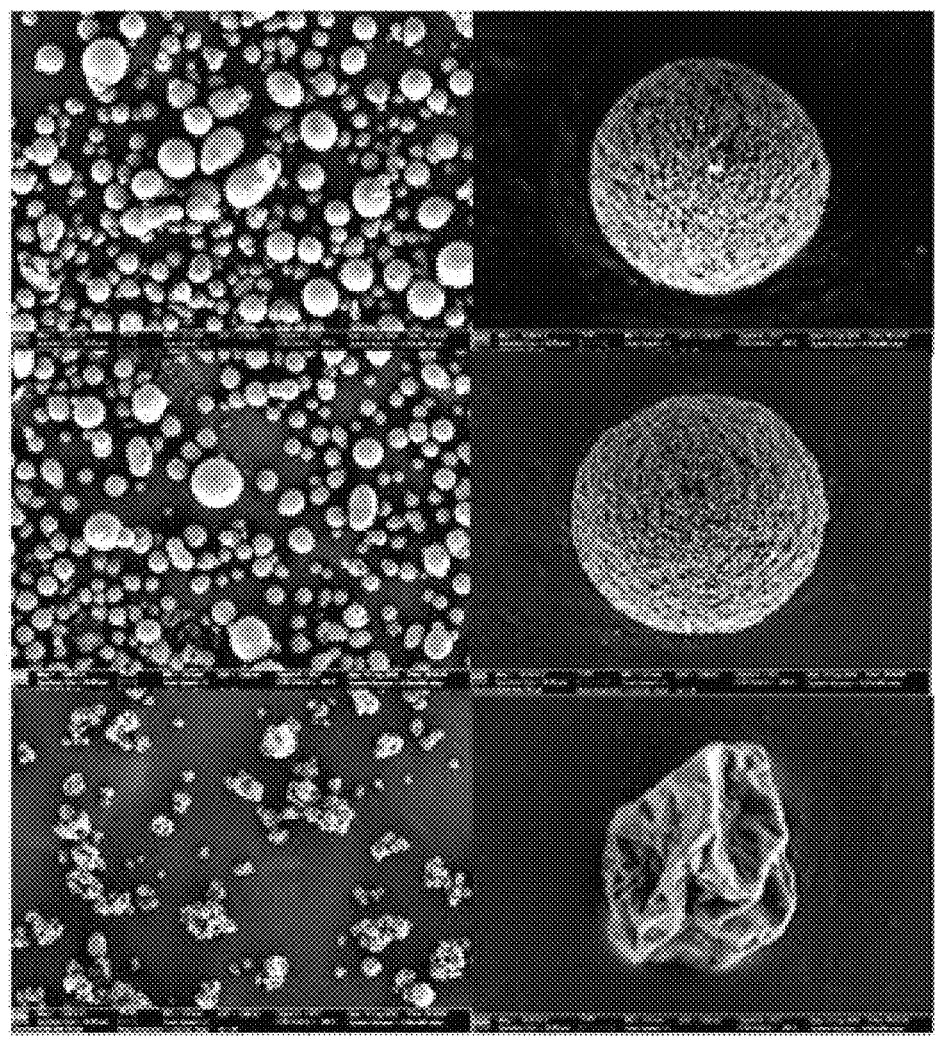
FIG. 4 shows the state of capsules after heat-treating the capsules, which are prepared by varying the contents of polymer and pigment (Examples 1 to 3), in an oven at 100° C. for 1 hour (SEM).
Figure 5:
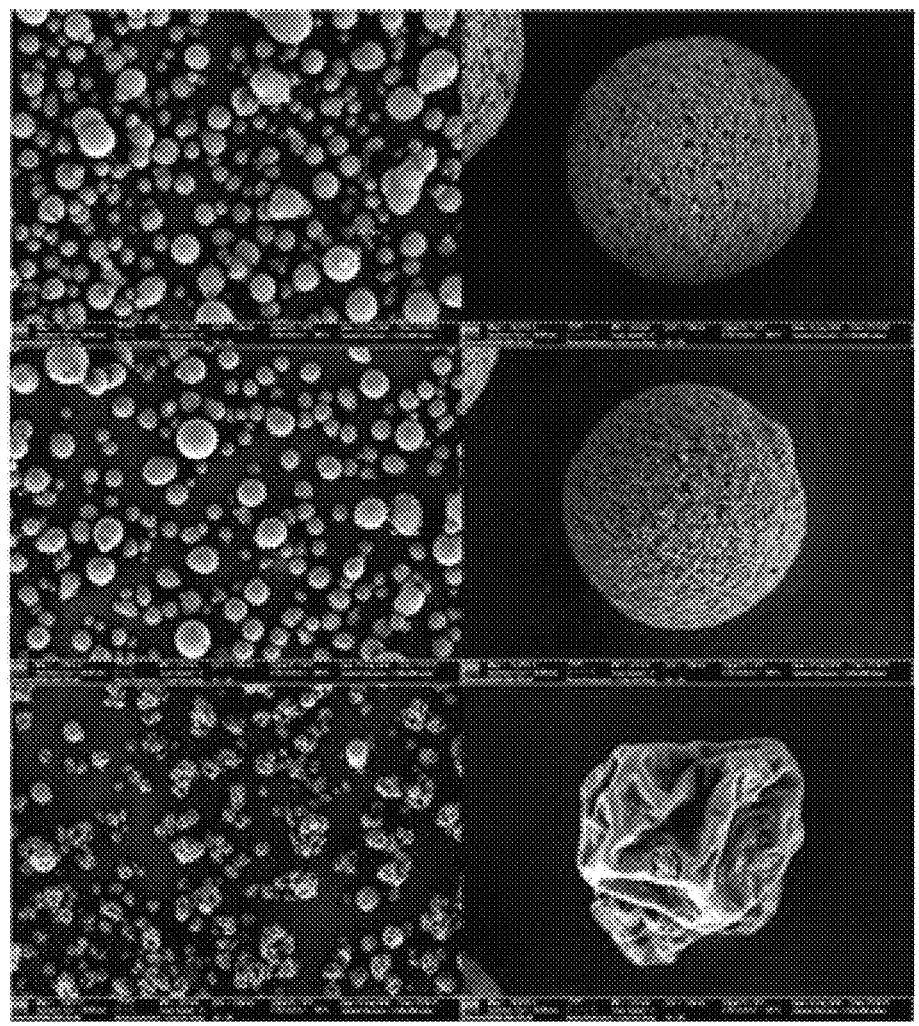
FIG. 5 shows the state of capsules after heat-treating the capsules, which are prepared by varying the contents of polymer and pigment (Examples 1 to 3), in an oven at 100° C. for 24 hour (SEM).

Specifically, the capsules of Examples 1 to 3 having different contents of polymer and pigment (polymer content of 10%+pigment content of 10%, polymer content of 20%+pigment content of 10%, polymer content of 20%+pigment content of 50%, respectively) were heat-treated in an oven at 100° C. for 1 hour or 24 hours, and then the capsule state was observed under a scanning electron microscope (SEM). Observation results are shown in Table 1, FIG. 4 (1-hour heat treatment) and FIG. 5 (24-hour heat treatment).

TABLE 1

|  | Polymer content of 10% + pigment content of 10%, | Polymer content of 20% + pigment content of 10% | Polymer content of 20% + pigment content of 50% |
|---|---|---|---|
| Heat treatment in an oven at 100° C. for 1 hour | As a result of SEM analysis, all of them were stable. | | |
| Heat treatment in an oven at 100° C. for 24 hours | | | |

As shown in Table 1, it can be confirmed that all pigment capsules prepared according to the present invention maintained the stability when the polymer was heat-treated at 100° C., which is a high temperature, for 1 hour or 24 hours.

Test Example 4

Evaluation of Hardness (Cracking or Breaking) of Pigment Capsules

The hardness (cracking or breaking) of the pigment capsules according to the present invention was confirmed by the following method.

Specifically, the capsules of Examples 1 to 3 having different contents of polymer and pigment (polymer content of 10%+pigment content of 10%, polymer content of 20%+pigment content of 10%, polymer content of 20%+pigment content of 50%, respectively) were rubbed with a hand once, 3 times or 7 times, then, it was confirmed whether or not the capsules crack or broke. The cracking or breakage of the capsules was confirmed through SEM.

Figure 6:
FIG. 6 shows whether the capsules are cracked or broken after rubbing the capsules, which are prepared by varying the contents of polymer and pigment (Examples 1 to 3), with a hand 1, 3 or 7 times (SEM).
Figure 6:
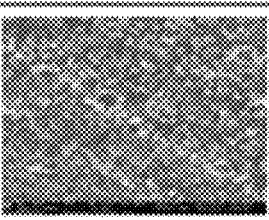
Figure 6:
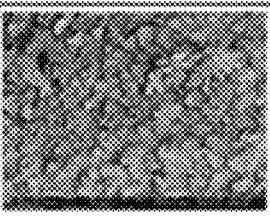
Figure 6:
Figure 6:
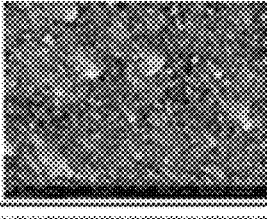
Figure 6:
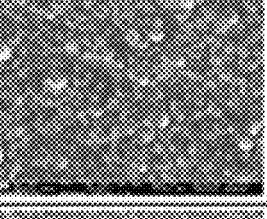
Figure 6:
Figure 6:
Figure 6:
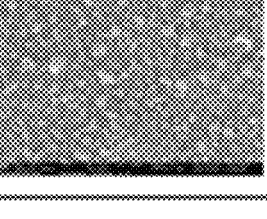

The evaluation results are shown in Table 2 and FIG. 6.

TABLE 2

|  | Polymer content of 10% + pigment content of 10%, | Polymer content of 20% + pigment content of 10% | Polymer content of 20% + pigment content of 50% |
|---|---|---|---|
| When rubbed with hand once | Not broken | Not broken | Not broken |
| When rubbed with hand 3 times | Broken | Broken | Not broken |
| When rubbed with hand 7 times | Broken | Broken | Broken |

As seen from the results of Table 2 and FIG. 6, the higher the content of the polymer binder, the higher the hardness, and thus the capsules did not easily crack or break, and when rubbed by hand 7 times, the capsules are all broken and the color development occurred, confirming allowing color development to easily occur on the skin when a user makes up without a specific tool or device.

Test Example 5

Figure 7:
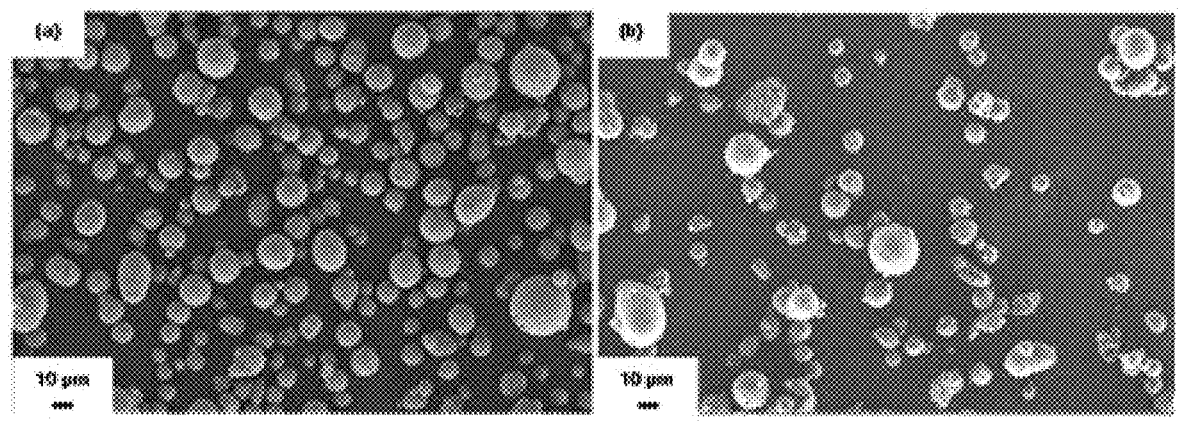
FIG. 7 confirms that the capsules are remained intact without being cracked or broken after the formulation test when the capsules were prepared into lipstick formulations (SEM).

Evaluation of Cracking or Breaking of Capsules Before and After Lipstick Formulation Test When the capsules were prepared into lipstick formulations, it was confirmed that the capsules remained intact after formulation testing without breakage (see, FIG. 7).

Test Example 6

Figure 8A:
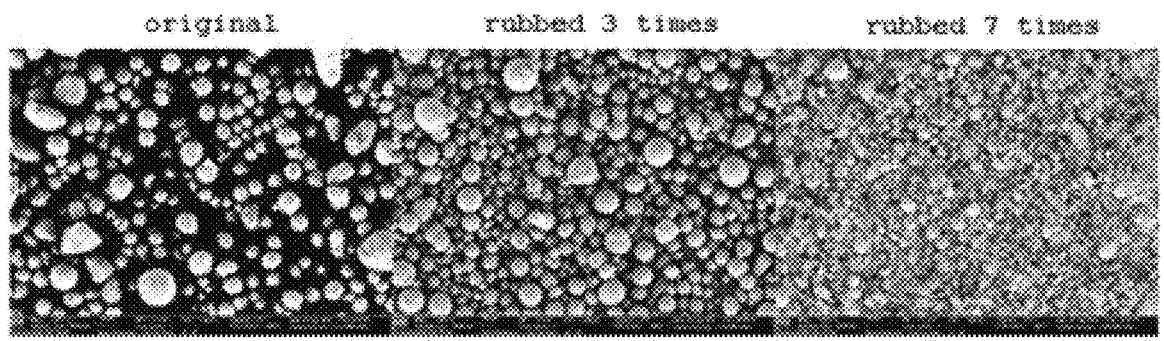
FIG. 8(A) confirms the cracking or breaking of the capsules when the polymer type is varied or the capsule exterior is altered (SEM). Here, (a) of FIG. 8(B) is an image before rubbing porous silica supported with iron oxide, and (b) of FIG. 8(B) is an image after rubbing it 7 times.
Figure 8B:
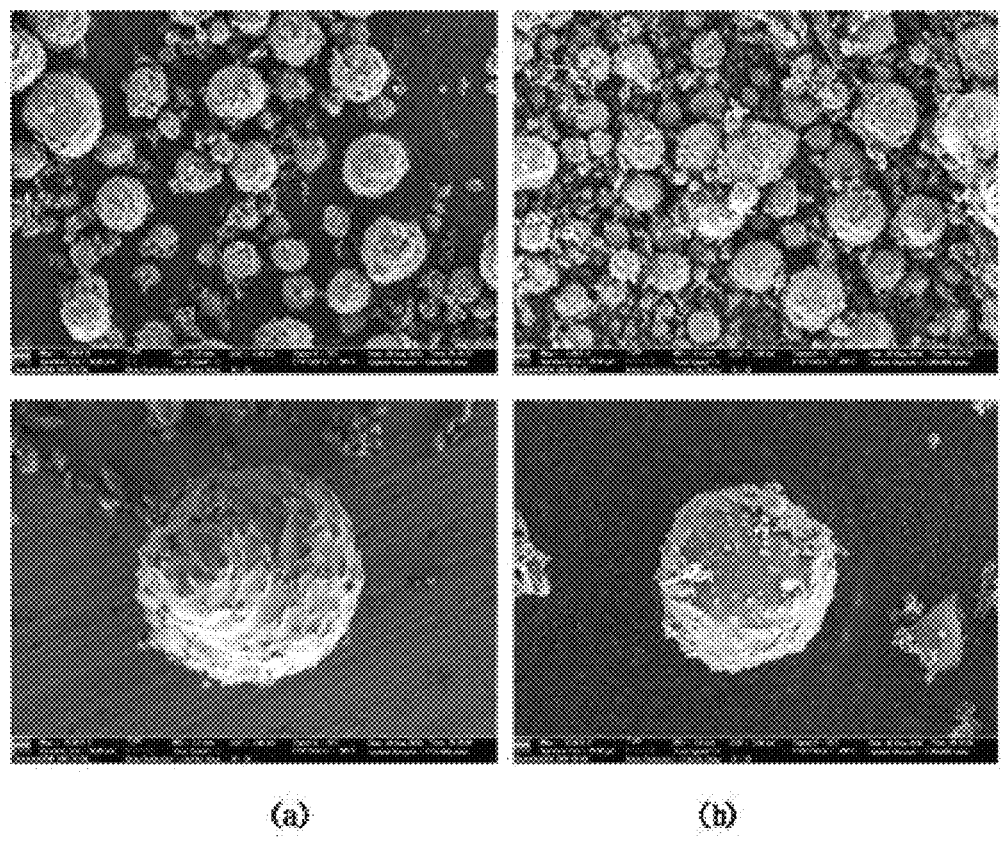

Evaluation of Cracking or Breaking of Capsules when the Polymer Type was Varied or the Capsule Exterior was Altered It was confirmed that the capsules did not crack or break even when rubbed by hand 7 times, when ethyl cellulose as a type of polymer was used, or silica supported with iron oxide was used (see, FIG. 8).

Test Example 7

Observation of Expression of Exterior Color and Tinting Strength on Skin of Capsules Lipstick formulations containing the pigment capsules according to the present invention were prepared with the compositions of Table 3 below. Formulation (a) contains non-encapsulated Red 27, Formulations (b) to (d) contain encapsulated Red 27. In particular, Formulation (b) contains 10% of Red 27+5% of polymer, Formulation (c) contains 10% of Red 27+5% of polymer+1% of citric acid, and Formulation (d) contains 10% of Red 27+5% of polymer+5% of citric acid.

Figure 9:
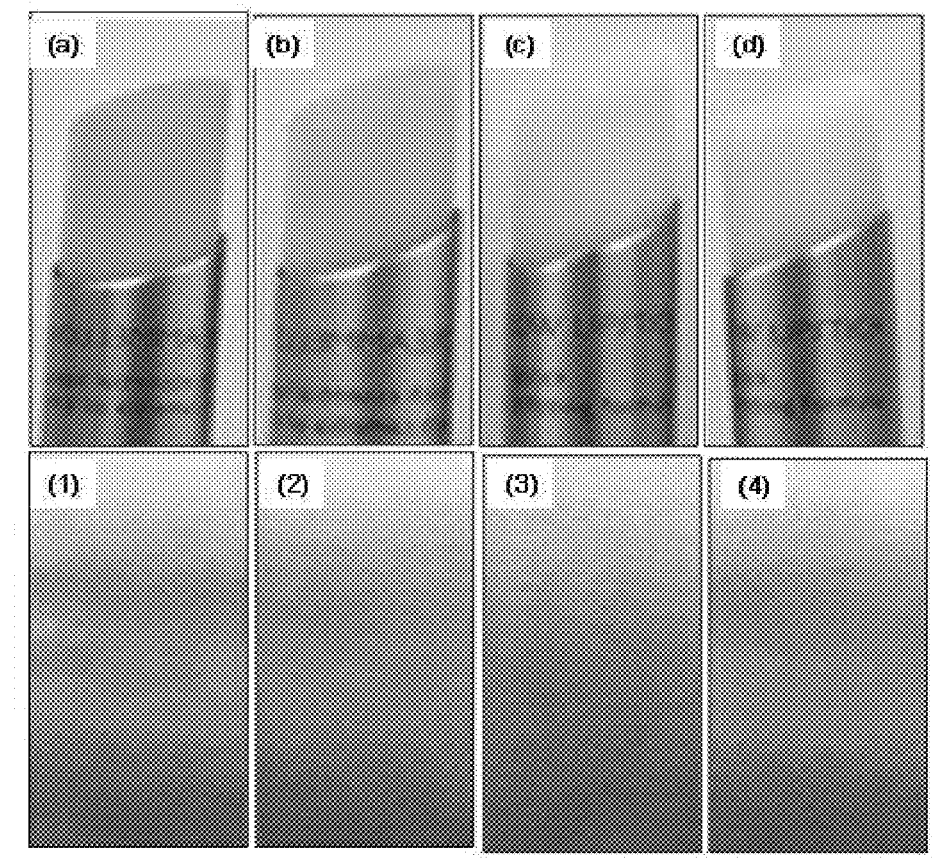
FIG. 9 shows the exterior of formulations including pigment capsules having various compositions.

The lipstick formulations prepared with the above compositions were applied to the skin of the back of the hand, and the degree of color development was observed. The results of the expression of exterior color and tinting strength on the skin of the polymer capsules are shown in FIG. 9.

TABLE 3

(unit: wt %)

| | Formulation (a) | Formulation (b) | Formulation (c) | Formulation (d) |
|---|---|---|---|---|
| Polyethylene | 15.0 | 15.0 | 15.0 | 15.0 |
| Distearyl malate | 30.0 | 30.0 | 30.0 | 30.0 |
| Vaseline | 20.0 | 20.0 | 20.0 | 20.0 |
| Caprylic/capric triglyceride | 15.0 | 15.0 | 15.0 | 15.0 |
| Red 27 | 0.1 | — | — | — |
| Capsule | — | 1.0 | 1.0 | 1.0 |

Upon comparison of FIGS. 9(a) and (b) showing Formulation (a) containing non-encapsulated pigments and Formulation (b) containing encapsulated pigments, respectively, it can be seen that the expression of exterior color of the lipsticks could be suppressed only by encapsulating the pigments.

In addition, when citric acid was added to adjust the pH of the capsule interior to be acidic, the exterior color could be adjusted close to colorless as shown in FIGS. 9(c) and (d). In particular, it can be confirmed through FIG. 9(d) that using citric acid in an amount of 5% by weight was found to be the optimal condition.

Meanwhile, the result of application of Formulations (a) to (d) to the skin are shown in (1) to (4) at the bottom of FIG. 9, and it can be confirmed from the results that the tinting strength on the skin was maintained even when the exterior color of the formulations was suppressed.

Test Example 8

Observation of Expression of Exterior Color of Capsules According to Content of Citric Acid Lipstick formulations containing the pigment capsules according to the present invention were prepared with the compositions of Table 4 below. Formulation (a) contains the capsule of Example 4, Formulation (b) contains the capsule of Example 5, Formulation (c) contains the capsule of Example 6, and Formulation (d) contains the capsule of Example 7.

TABLE 4

(unit: wt %)

| | Formulation (a) | Formulation (b) | Formulation (c) | Formulation (d) |
|---|---|---|---|---|
| Polyethylene | 15.0 | 15.0 | 15.0 | 15.0 |
| Distearyl malate | 30.0 | 30.0 | 30.0 | 30.0 |
| Vaseline | 20.0 | 20.0 | 20.0 | 20.0 |
| Caprylic/capric triglyceride | 15.0 | 15.0 | 15.0 | 15.0 |
| Red 27 | 0.1 | — | — | — |
| Capsule | — | 1.0 | 1.0 | 1.0 |

The exterior of the lipstick formulations prepared with the above compositions was observed, and the degree of exterior color change according to the content of citric acid was observed. The results are shown in FIG. 10.

Figure 10:
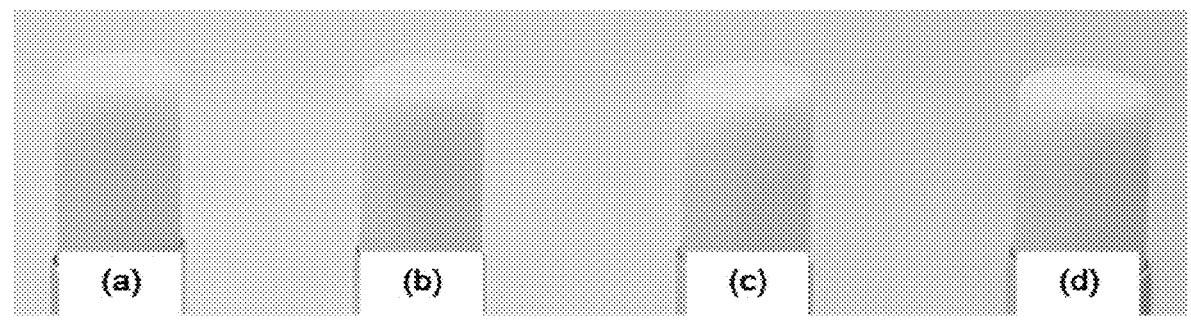
FIG. 10 shows the exterior of formulations including pigment capsule according to the content of citric acid.

As shown in FIG. 10, when the content of Red 27 Lake was constant, the exterior color of the formulations did not significantly change even when the content of citric acid was increased.

Based on the results, it can be seen that when the content of citric acid reached a certain concentration level, the role of citric acid in color change was not significant.

Figure 11:
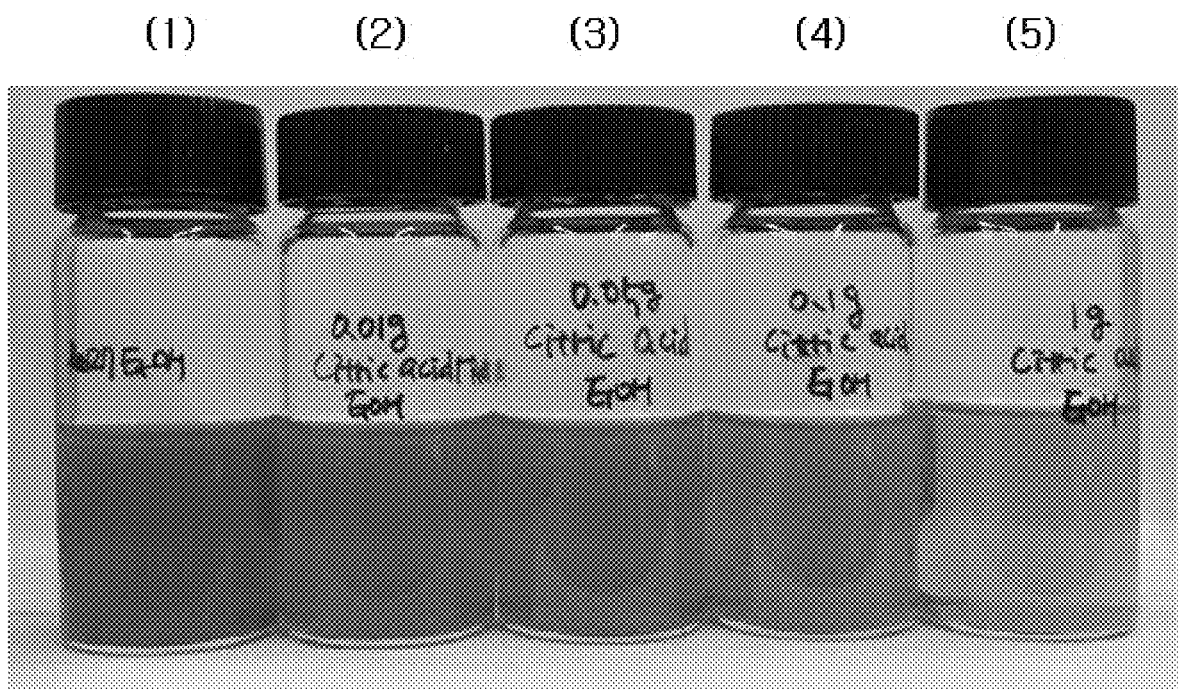
FIG. 11 shows the degree of color change of the pigment according to the content of citric acid ((1) ethanol only; (2) ethanol+0.01 g of citric acid; (3) ethanol+0.05 g of citric acid; (4) ethanol+0.1 g of citric acid; (5) ethanol+1 g of citric acid).

Meanwhile, in order to confirm the degree of color change by citric acid in the non-encapsulated pigments, 0.01 g of Red 27 Lake was dissolved in 10 ml of EtOH, and then 0 g, 0.01 g, 0.05 g, 0.1 g and 1 g of citric acid was added (corresponding to FIG. 11 (1) to (5), respectively), and the color change of Red 27 Lake was observed. The results are shown in FIG. 11.

As shown in FIG. 11, it can be confirmed that when 0.01 g, 0.05 g and 0.1 g of citric acid was added, respectively, relative to the equivalent amount of Red 27 Lake, the color of Red 27 Lake appeared almost the same.

Test Example 9

Observation of Expression of Exterior Color and Tinting Strength on Skin According to Presence or Absence of Red 27 in Formulations A lipstick formulation containing no pigment (Formulation 1), a lipstick formulation containing the pigment capsule (Red 27 Lake) according to the present invention (Formulation 2), and a lipstick formulation containing a non-encapsulated Red 27 Lake (Formulation 3) were prepared with the compositions of Table 5.

TABLE 5

(unit: wt %)

| | Formulation 1 | Formulation 2 | Formulation 3 |
|---|---|---|---|
| Polyethylene | 15.0 | 15.0 | 15.0 |
| Distearyl malate | 30.0 | 30.0 | 30.0 |
| Vaseline | 20.0 | 20.0 | 20.0 |
| Caprylic/capric triglyceride | 15.0 | 15.0 | 15.0 |
| RED 7 LAKE (CI 15850:1) | 2.0 | 2.0 | 2.0 |
| YELLOW 6 LAKE (CI 15985) | 3.5 | 3.5 | 3.5 |
| IRON OXIDES (CI 77491) | 3.5 | 3.5 | 3.5 |
| Red 27 | — | — | 0.1 |
| Capsule | — | 1.0 | — |

The lipstick formulations prepared with the above compositions were applied to the skin of the back of the hand, and the degree of color development was observed. The results of the expression of exterior color and tinting strength on the skin of the polymer capsules are shown in FIG. 12.

Figure 12:
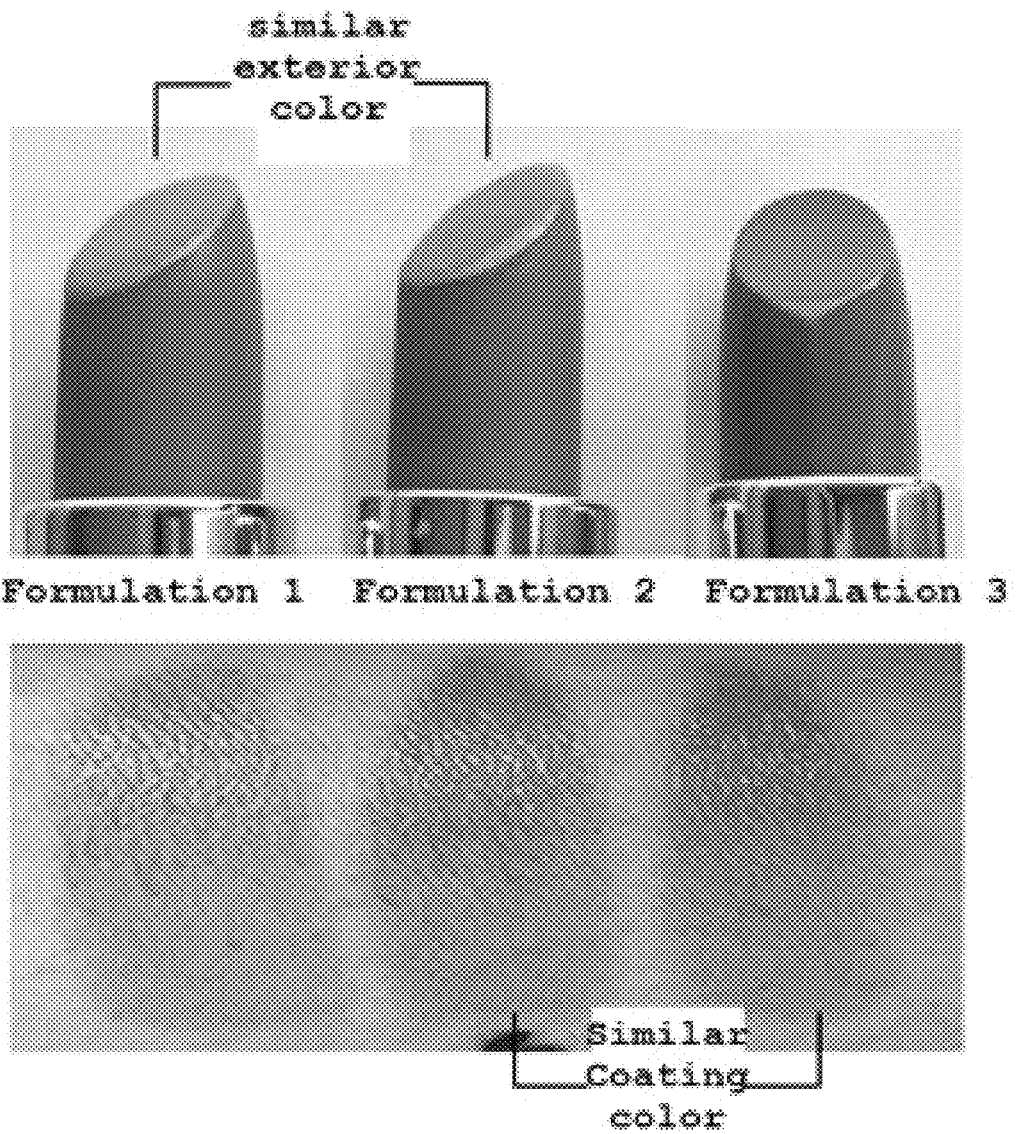
FIG. 12 shows the appearance of formulations containing pigment capsules or non-encapsulated pigments. The exterior color of lipstick in Formulation 2 does not appear to be reddish, but it appears reddish when applied to the skin.

As shown in FIG. 12, it was confirmed that the formulation containing the encapsulated pigment according to the present invention (Formulation 2) showed an exterior color identical to that of the control lipstick containing no pigment (Formulation 1), and also showed excellent color developing ability on the skin identical to the formulation containing the non-capsulated Red 27 dye (Formulation 3).

The invention claimed is:

1. A pigment capsule comprising a pigment,
    wherein the pigment capsule has an interior in which all of silica, the pigment, a titanium dioxide, and a $C_3$-$C_9$ trivalent carboxylic acid are dispersed, and an exterior covered with a polymer binder having a glass transition temperature of 130° C. or higher, and
    wherein the polymer binder is an acrylate copolymer,
    wherein the $C_3$-$C_9$ trivalent carboxylic acid is one or more selected from the group consisting of citric acid, isocitric acid, aconitic acid, tricarballylic acid, and trimesic acid,
    wherein a content of the pigment is 10 to 50% by weight based on the total weight of the capsule.

2. The pigment capsule of claim 1, wherein a content of the polymer binder is 5 to 20% by weight based on the total weight of the capsule.

3. The pigment capsule of claim 1, wherein the capsule has an average diameter of 15 to 25 μm.

4. A method for producing a pigment capsule of claim 1, comprising the steps of:
    1) dissolving a polymer binder and a $C_3$-$C_9$ trivalent carboxylic acid in a first solvent and dissolving a pigment in a second solvent, respectively, and then mixing them to give a mixed polymer solution;
    2) adding silica and titanium dioxide to the mixed polymer solution obtained in step 1), and dispersing the resulting mixture; and
    3) spray drying the mixture obtained in step 2) to obtain spray-dried pigment/polymer binder composite powder particles as the pigment capsule,
    wherein the polymer binder is an acrylate copolymer having a glass transition temperature of 130° C. or higher,
    wherein the $C_3$-$C_9$ trivalent carboxylic acid is at least one selected from the group consisting of citric acid, isocitric acid, aconitic acid, tricarballylic acid, and trimesic acid,
    wherein the pigment capsule has an interior in which all of the silica, pigment, titanium dioxide pigment, and the $C_3$-$C_9$ trivalent carboxylic acid are dispersed, and an exterior covered with the polymer binder, and
    wherein a content of the pigment is 10 to 50% by weight based on the total weight of the capsule.

5. The method for producing a pigment capsule of claim 4, wherein the first solvent is one or more organic solvent selected from the group consisting of a $C_1$-$C_4$ lower alcohol, acetone, and a mixture thereof, or a mixture of the organic solvent and water.

6. The method for producing a pigment capsule of claim 4, wherein the second solvent is a chlorine-containing hydrocarbon-based solvent.

7. The method for producing a pigment capsule of claim 4, wherein the ratio of the first solvent used to dissolve the polymer and the second solvent used to dissolve the pigment is 3:7.

8. The pigment capsule of claim 1, wherein the pigment is selected from the group consisting of:
    D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, 20 D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6, and a combination thereof.

9. The pigment capsule of claim 1, wherein the pigment is D&C Red 27, D&C Red 28, or a combination thereof.

10. A lip makeup formulation comprising the pigment capsule of claim 1.

11. A lip makeup formulation comprising the pigment capsule of claim 2.

12. A lip makeup formulation comprising the pigment capsule of claim 3.

13. A lip makeup formulation comprising the pigment capsule of claim 8.

14. A lip makeup formulation comprising the pigment capsule of claim 9.

* * * * *